(12) United States Patent
Wang et al.

(10) Patent No.: US 7,993,046 B2
(45) Date of Patent: Aug. 9, 2011

(54) FLEXIBLE LIGHT-EMITTING APPARATUS

(75) Inventors: Chiang-Ching Wang, Miaoli County (TW); Chi-Wen Kuo, Tainan (TW); Jun-Zhou Chen, Hsinchu (TW); Chien-Hua Wu, Miaoli County (TW); Tsung-Hsien Chou, Hsinchu (TW); Chia-Hung Hsu, Taipei County (TW)

(73) Assignee: United Lighting Opto-Electronic Inc., Hsinchu (TW)

( * ) Notice: Subject to any disclaimer, the term of this patent is extended or adjusted under 35 U.S.C. 154(b) by 212 days.

(21) Appl. No.: 12/426,962

(22) Filed: Apr. 21, 2009

(65) Prior Publication Data

US 2010/0238683 A1    Sep. 23, 2010

(30) Foreign Application Priority Data

Mar. 17, 2009   (TW) .............................. 98204197 U (51) Int. Cl.
*F21V 7/04*     (2006.01)
*H01L 33/00*   (2010.01)

(52) U.S. Cl. .................... 362/555; 362/249.02; 362/800

(58) Field of Classification Search ............. 362/249.02, 362/555, 800
See application file for complete search history.

(56) References Cited

U.S. PATENT DOCUMENTS

2004/0085762 A1 * 5/2004 Iwasa et al. .................... 362/217
2009/0052205 A1 * 2/2009 Chen et al. ..................... 362/612

* cited by examiner

*Primary Examiner* — Jason Moon Han
(74) *Attorney, Agent, or Firm* — Jianq Chyun IP Office (57) ABSTRACT

A flexible light-emitting apparatus including a side light-emitting flexible light guide rod, two light emitting diodes, and two lenses is provided. The side light-emitting flexible light guide rod has a first end, a second end opposite to the first end, and a light-emitting surface connecting the first and the second ends. The LEDs are respectively disposed beside the first end and the second end and adapted for emitting light beams toward the side light-emitting flexible light guide rod, respectively. One of the lenses is located between the first end and the LED disposed beside the first end, and the other lens is located between the second end and the LED disposed beside the second end. Each of the light beams enters the side light-emitting flexible light guide rod through the corresponding lens and is transmitted to the outside of the side light-emitting flexible light guide rod through the light-emitting surface.

14 Claims, 12 Drawing Sheets

FLEXIBLE LIGHT-EMITTING APPARATUS

CROSS-REFERENCE TO RELATED APPLICATION

This application claims the priority benefit of Taiwan application serial no. 98204176, filed on Mar. 17, 2009. The entirety of the above-mentioned patent application is hereby incorporated by reference herein and made a part of specification.

BACKGROUND OF THE INVENTION

1. Field of Invention

The present invention generally relates to a light-emitting apparatus, and more particularly, to a flexible light-emitting apparatus with uniform brightness.

2. Description of Related Art

Since luminance of a light emitting diode (LED) has been increasing in recent years, the LED is gradually replacing a traditional light source in many fields. The luminance of the LED does not result from thermal light emission or electric discharge but from cold light emission, and therefore the life span of the LED is more than 100,000 hours. In addition, the LED also has advantages of highly short responsive time (about $10^{-9}$ S), small size, low power consumption, little pollution, high reliability, being adapted for mass production, and so on. Accordingly, the LED can be widely used in many fields. However, the LED is a point light source and has high directionality, so that light beams emitted from the LEDs are highly focused, and brightness of the LED is concentrated. Accordingly, applications of the LEDs are limited. Therefore, one of the main issues lies in how to guide the focused light beams uniformly as the LED light-emitting apparatus is highly developed.

Figure 1:
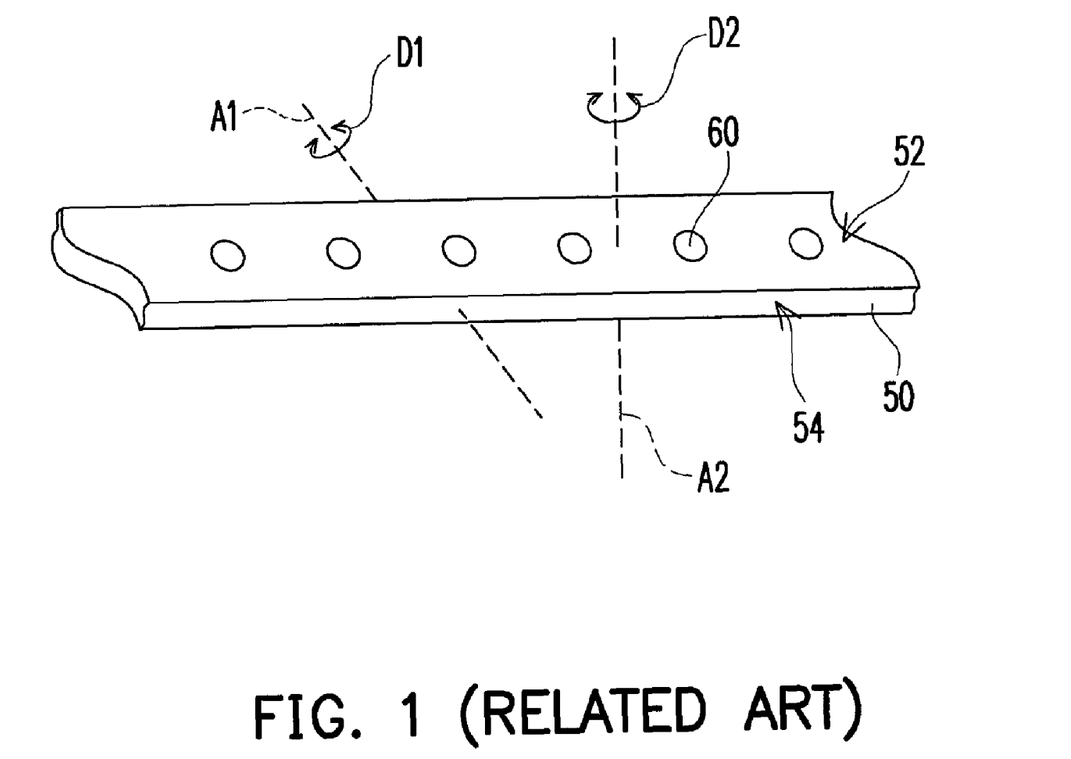
FIG. 1 is a three-dimensional view of a flexible printed circuit board and LEDs of a conventional flexible LED neon lamp.

FIG. 1 is a three-dimensional view of a flexible printed circuit board and LEDs of a conventional flexible LED neon lamp. Referring to FIG. 1, the conventional flexible LED neon lamp utilizes the flexible printed circuit board 50 to support the LEDs 60 with a single color or different colors. Moreover, the flexible printed circuit board 50 and the LEDs 60 are surrounded by a diffusion layer, so that the light beams emitted from the LEDs 60 are uniform.

However, since the flexible printed circuit board 50 is a plate, it is easy to be bended from a direction of the width parallel to an axis A1 to a direction D1, but it is not easy to be bended from a direction of the thickness parallel to an axis A2 to a direction D2. The flexibility of the conventional flexible LED neon lamp is thus highly limited due to the above-described phenomenon. Besides, since the LEDs 60 are only disposed on a surface 52 but not disposed on a surface 54, the light-emitting direction of the conventional flexible LED neon lamp is highly limited, so that applications and the flexibility of the conventional flexible LED neon lamp is significant restricted.

SUMMARY OF THE INVENTION

One embodiment of the present invention provides a flexible light-emitting apparatus which has a superior flexibility, uniform luminance, and few restrictions on a light-emitting direction.

One embodiment of the present invention provides a flexible light-emitting apparatus including a side light-emitting flexible light guide rod, two LEDs, and two lenses. The side light-emitting flexible light guide rod has a first end, a second end opposite to the first end, and a light-emitting surface connecting the first and the second ends. The two LEDs are respectively disposed beside the first end and the second end of the side light-emitting flexible light guide rod and adapted to emit a light beam toward the side light-emitting flexible light guide rod, respectively. One of the above-described lenses is located between the first end and the LED disposed beside the first end, and the other one of the above-described lenses is located between the second end and the LED disposed beside the second end. Each of the light beams respectively enters the side light-emitting flexible light guide rod through the corresponding lens and is transmitted to the outside of the side light-emitting flexible light guide rod through the light-emitting surface.

In an embodiment of the present invention, when the brightness of the LEDs is a half of the maximum brightness thereof, the view angle of the LEDs is not larger than 130 degrees.

In an embodiment of the present invention, the lenses have a function of focusing the light beams, and the focus lengths thereof are not longer than 20 millimeters.

In an embodiment of the present invention, a material of the lenses is glass, plastic, or resin.

In an embodiment of the present invention, a surface of each of the lenses is respectively evaporated with an optical thin film. The optical thin films are used to filter color light beams with predetermined wavelengths or let color light beams with predetermined wavelengths pass.

In an embodiment of the present invention, a distance between each of the lenses and the LED corresponding thereto is not longer than 1.5 millimeters.

In an embodiment of the present invention, the flexible light-emitting apparatus further includes two optical filters. Each of the optical filters is respectively disposed between one of the lenses and the LED corresponding thereto or between the lens and the side light-emitting flexible light guide rod.

In an embodiment of the present invention, a distance between each of the lenses and the side light-emitting flexible light guide rod is not longer than 1.5 millimeters.

In an embodiment of the present invention, the side light-emitting flexible light guide rod includes a light guide core and a light-emitting layer. The light guide core extends from the first end to the second end of the side light-emitting flexible light guide rod. The light-emitting layer surrounds the light guide core and extends from the first end to the second end of the side light-emitting flexible light guide rod. Here, an index of refraction of the light guide core relative to a visible light is larger than an index of refraction of the light-emitting layer relative to the visible light.

In an embodiment of the present invention, a material of the light guide core is a copolymer $MMA_xBMA_y3EGDM_{1-x-y}$ which is formed by methyl methacrylate (MMA), normal butyl (bornyl) methacrylate (BMA), and triethylene glycol dimethacrylate (3EGDMA) in different proportions, wherein x and y are positive numbers, and $0.22 \leq x \leq 0.35$ and $0.45 \leq y \leq 0.63$.

In an embodiment of the present invention, a material of the light-emitting layer is tetra-fluoro-ethylene, perfluoro-alkoxy or fluorinated propylene ethylene.

In an embodiment of the present invention, grains of methyl methacrylate styrene (MS) having a diameter of 6-15 micrometers and a weight percentage of 0.01%-0.03% are doped into and uniformly distributed in the light guide core.

In an embodiment of the present invention, the light-emitting layer has color powders.

In an embodiment of the present invention, the flexible light-emitting apparatus further two package housings, and each of the package housings is respectively used to house one of the LEDs and the lens corresponding thereto.

In an embodiment of the present invention, the flexible light-emitting apparatus further includes two mounting bases. Each of the mounting bases is respectively connected to the corresponding package housing, so that the package housings are fixed onto a foundation by appropriately bending the mounting bases, wherein heat generated by the LEDs is released through the foundation to the environment.

In an embodiment of the present invention, each of the mounting bases is integrally formed with the corresponding package housing.

In view of the above, the flexible light-emitting apparatus of the embodiment of the present invention utilizes the side light-emitting flexible light guide rod to guide light beams, and the LEDs are respectively disposed beside the two ends of the side light-emitting flexible light guide rod. Since the side light-emitting flexible light guide rod is a rod, it is able to be bended in any direction perpendicular to an extending direction of the side light-emitting flexible light guide rod, so that the side light-emitting flexible light guide rod has better flexibility. Moreover, since light beams emitted from the LEDs are uniformly radiated from the light-emitting surface of the side light-emitting flexible light guide rod, the light-emitting directions of the flexible light-emitting apparatus are less limited.

In order to make the aforementioned and other features and advantages of the present invention more comprehensible, one embodiment accompanied with figures is described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 2:
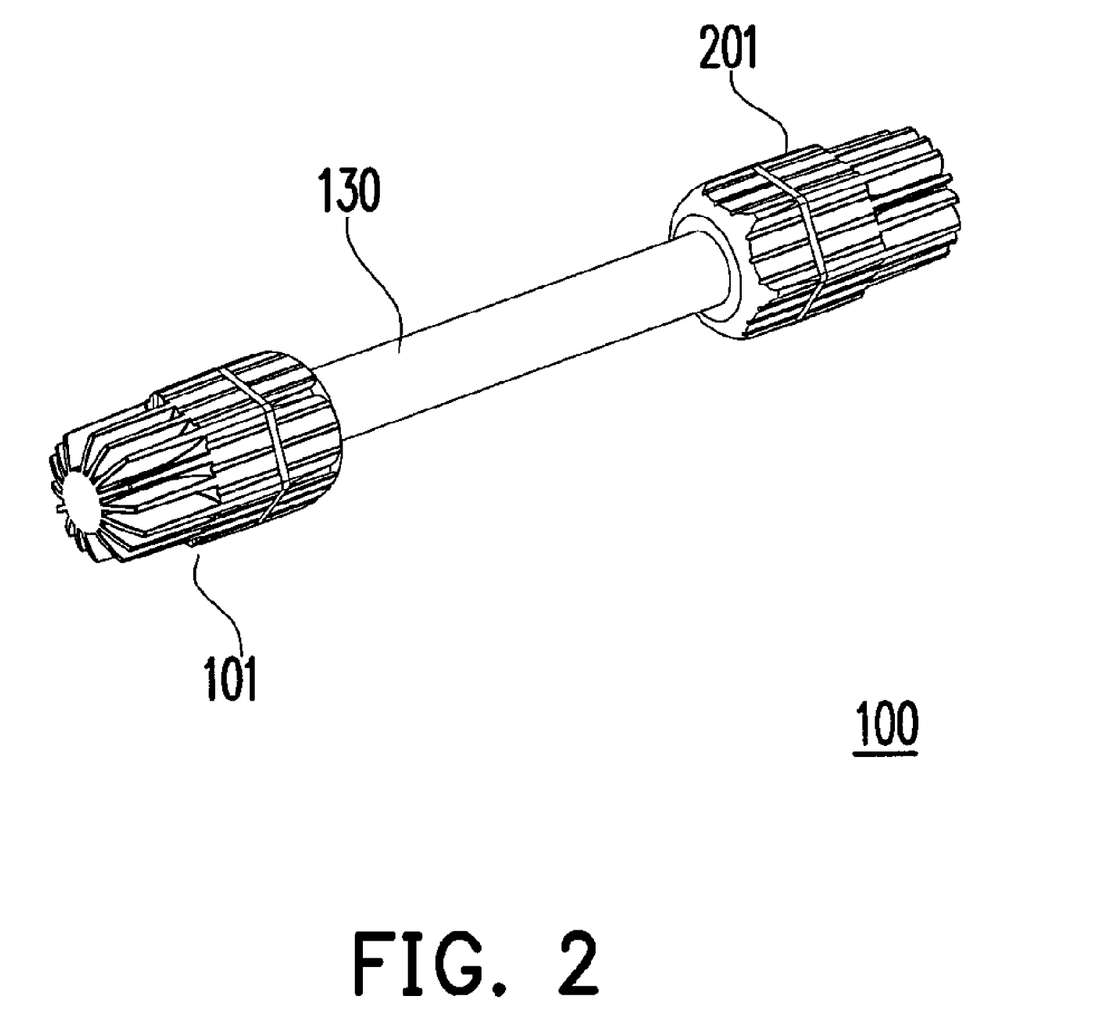
FIG. 2 is a three-dimensional view of a flexible light-emitting apparatus according to an embodiment of the present invention.

FIG. 2 is a three-dimensional view of a flexible light-emitting apparatus according to an embodiment of the present invention. Referring to FIG. 2, the flexible light-emitting apparatus 100 includes a side light-emitting flexible light guide rod 130, LEDs 110 and 210, lenses 120 and 220, and package housings 101 and 201.

In the present embodiment, the package housings 101 and 201 are respectively disposed at two ends of the side light-emitting flexible light guide rod 130 for housing the LEDs 110 and 210 and the lenses 120 and 220 and for collectively clamping the side light-emitting flexible light guide rod 130. Particularly, after the package housings 101 and 201 and the side light-emitting flexible light guide rod 130 are assembled, while the flexible light-emitting apparatus 100 is bended to be in a certain shape, centers of the package housings 101 and 201 and the side light-emitting flexible light guide rod 130 stay on a light axis without being shifted. Besides, the side light-emitting flexible light guide rod 130, the LEDs 110 and 210, and the lenses 120 and 220 together constitute a light source module.

Figure 3:
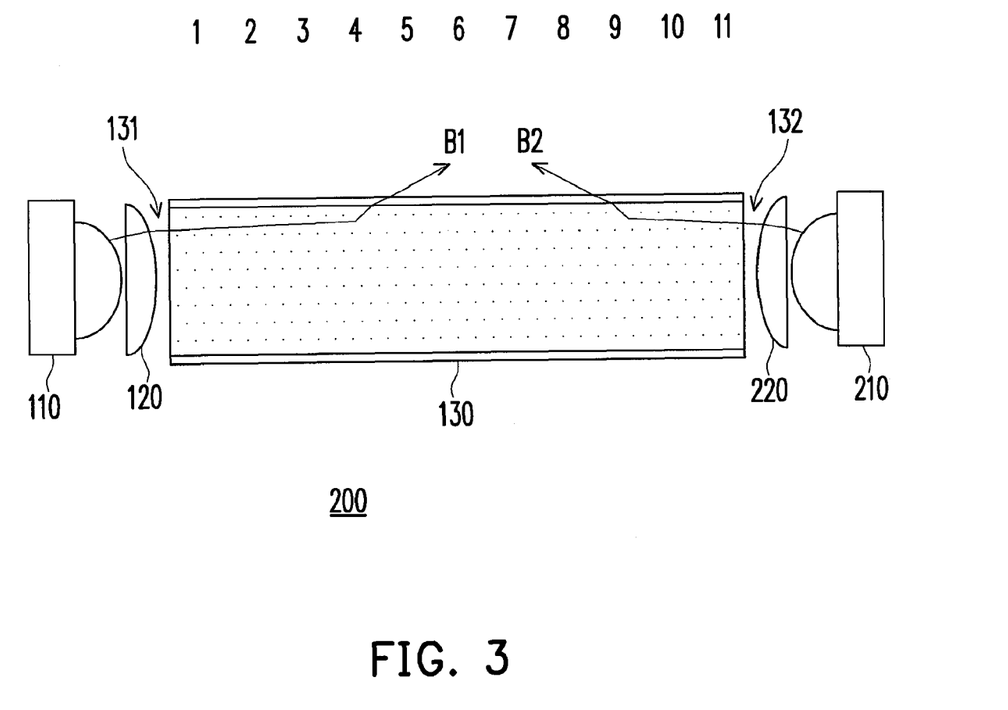
FIG. 3 is a schematic view of a light source module according to an embodiment of the present invention.
Figure 4:
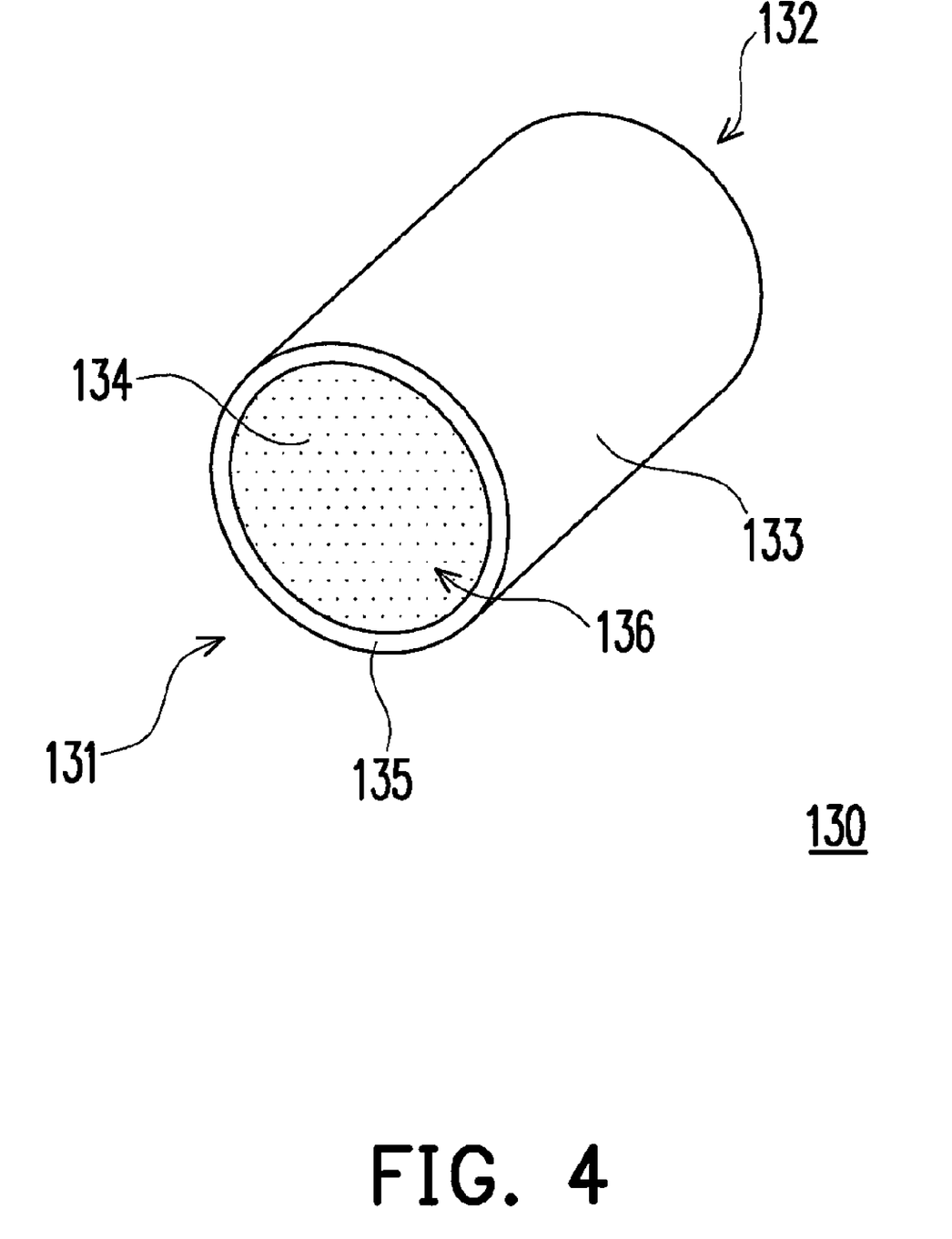
FIG. 4 is a schematic view of the side light-emitting flexible light guide rod of the light source module depicted in FIG. 3.

FIG. 3 is a schematic view of a light source module according to an embodiment of the present invention, and FIG. 4 is a schematic view of the side light-emitting flexible light guide rod of the light source module depicted in FIG. 3. Referring to FIGS. 3 and 4 simultaneously, the light source module 200 of the present embodiment includes the side light-emitting flexible light guide rod 130, the LEDs 110 and 210, and the lenses 120 and 220.

In the present embodiment, the side light-emitting flexible light guide rod 130 has a first end 131, a second end 132 opposite to the first end 131, and a light-emitting surface 133 connecting the first end 131 and the second end 132. The LED 110 is disposed beside the first end 131, and the lens 120 is disposed between the LED 110 and the first end 131. Here, a distance between the lens 120 and the LED 110 is not longer than 1.5 millimeters, and a distance between the lens 120 and the side light-emitting flexible light guide rod 130 is not longer than 1.5 millimeters. The LED 110 is adapted to emit a light beam B1 toward the lens 120. The light beam B1 passes through the lens 120 and the first end 131, enters the side light-emitting flexible light guide rod 130 from the first end 131, and is transmitted to the outside of the side light-emitting flexible light guide rod 130 through the light-emitting surface 133.

Similarly, the LED 210 is disposed beside the second end 132, and the lens 220 is disposed between the LED 210 and the second end 132. Here, a distance between the lens 220 and the LED 210 is not longer than 1.5 millimeters, and a distance between the lens 220 and the side light-emitting flexible light guide rod 130 is not longer than 1.5 millimeters. The LED 210 is adapted to emit a light beam B2 toward the lens 220. The light beam B2 passes through the lens 220 and the second end 132, enters the side light-emitting flexible light guide rod 130 from the second end 132, and is transmitted to the outside of the side light-emitting flexible light guide rod 130 through the light-emitting surface 133. In the present embodiment, the lenses 110 and 220 have a function of focusing the light beams, and the focus lengths of the lenses 110 and 220 are not longer than 20 millimeters. Besides, a material of the lenses 120 and 220 is glass, plastic, or resin, for example.

Referring to FIG. 4, in the present embodiment, the side light-emitting flexible light guide rod 130 includes a light guide core 134 and a light-emitting layer 135. The light guide core 134 extends from the first end 131 to the second end 132 of the side light-emitting flexible light guide rod 130. The light-emitting layer 135 surrounds the light guide core 134 and extends from the first end 131 to the second end 132. An index of refraction of the light guide core 134 relative to a visible light is larger than an index of refraction of the light-emitting layer 135 relative to the visible light, so that parts of the light beams B1 and B2 are able to be transmitted to the light-emitting layer 135. As a result, the light beams B1 and B2 pass through the light-emitting surface 133 from the light-emitting layer 135 and are transmitted to the outside of the side light-emitting flexible light guide rod 130. Besides, in the present embodiment, the light guide core 134 has tiny polymer grains 136 which are uniformly distributed therein. An index of refraction of the tiny polymer grains 136 relative to the visible light is different from that of the light guide core 134. The tiny polymer grains 136 can change the transmitting direction of the incident light beams B1 and B2, so that the light beams B1 and B2 enter the light-emitting layer 135, pass through the light-emitting surface 133 from the light-emitting layer 135, and are transmitted to the outside of the side light-emitting flexible light guide rod 130.

In the present embodiment, a material of the light guide core 134 is a copolymer $MMA_xBMA_y3EGDMA_{1-x-y}$, which is formed by methyl methacrylate (MMA), normal butyl (bornyl) methacrylate (BMA), and triethylene glycol dimethacrylate (3EGDMA) in different proportions, wherein x and y are positive numbers, and $0.22 \leq x \leq 0.35$ and $0.45 \leq y \leq 0.63$. Moreover, the tiny polymer grains 136 doped in the light guide core 134, for example, are grains of methyl methacrylate styrene (MS) having a diameter of 6-15 micrometers and a weight percentage of 0.01%-0.03% and are uniformly distributed therein. Besides, a material of the light-emitting layer 135, for example, is tetra-fluoro-ethylene, perfluoro-alkoxy, or fluorinated propylene ethylene.

Figure 5A:
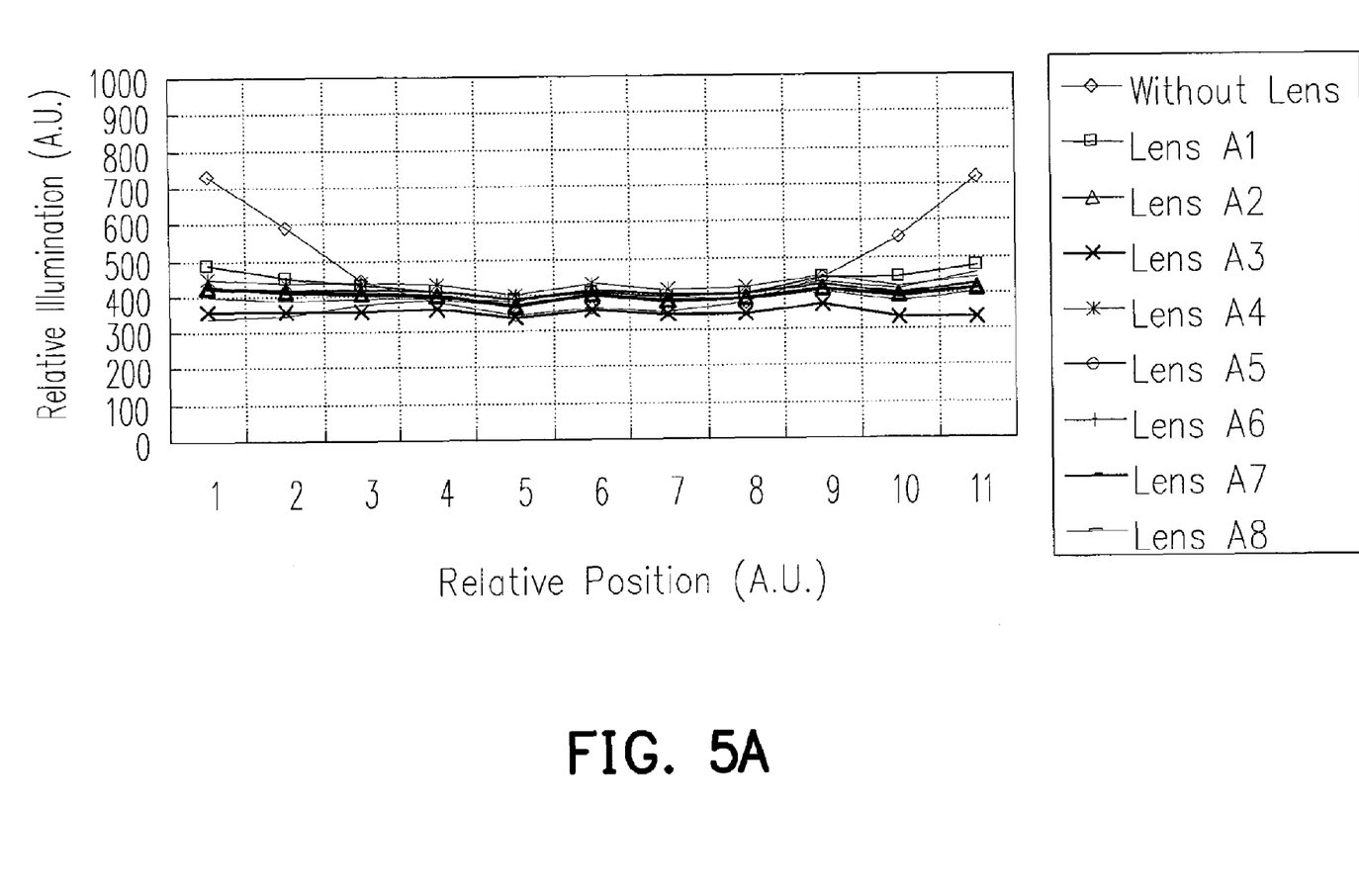
FIGS. 5A-5D are diagrams showing illumination distributions of the light source module depicted in FIG. 3 at relative positions 1-11. The illumination distributions of FIGS. 5A-5D are respectively obtained by measuring the illumination of the light source module, and the light source module has the LEDs with different view angles and the lenses of different types.

FIGS. 5A-5D are diagrams showing illumination distributions of the light source module depicted in FIG. 3 at relative positions 1-11. The illumination distributions of FIGS. 5A-5D are respectively obtained by measuring the illumination of the light source module, and the light source module have the LEDs with different view angles and the lenses of different types. Referring to FIGS. 3 and 5A-5D simultaneously, FIG. 5A is a diagram showing the illumination distributions obtained by measuring the illumination at the relative positions 1-11 while the light source module 200 depicted in FIG. 3 has the LEDs with a view angle of 25 degrees and the lenses A1, A2, A3, A4, A5, A6, A7, and A8 of different types.

For example, a data point M1 of FIG. 5A is an illumination value measured at the relative position 10 while the lenses 120 and 220 are the same-type lenses A3. A data point M2 of FIG. 5A is an illumination value measured at the relative position 2 while the lenses 120 and 220 are not disposed at the two ends 131 and 132 of the side light-emitting flexible light guide rod 130 in the light source module 200.

Figure 5B:
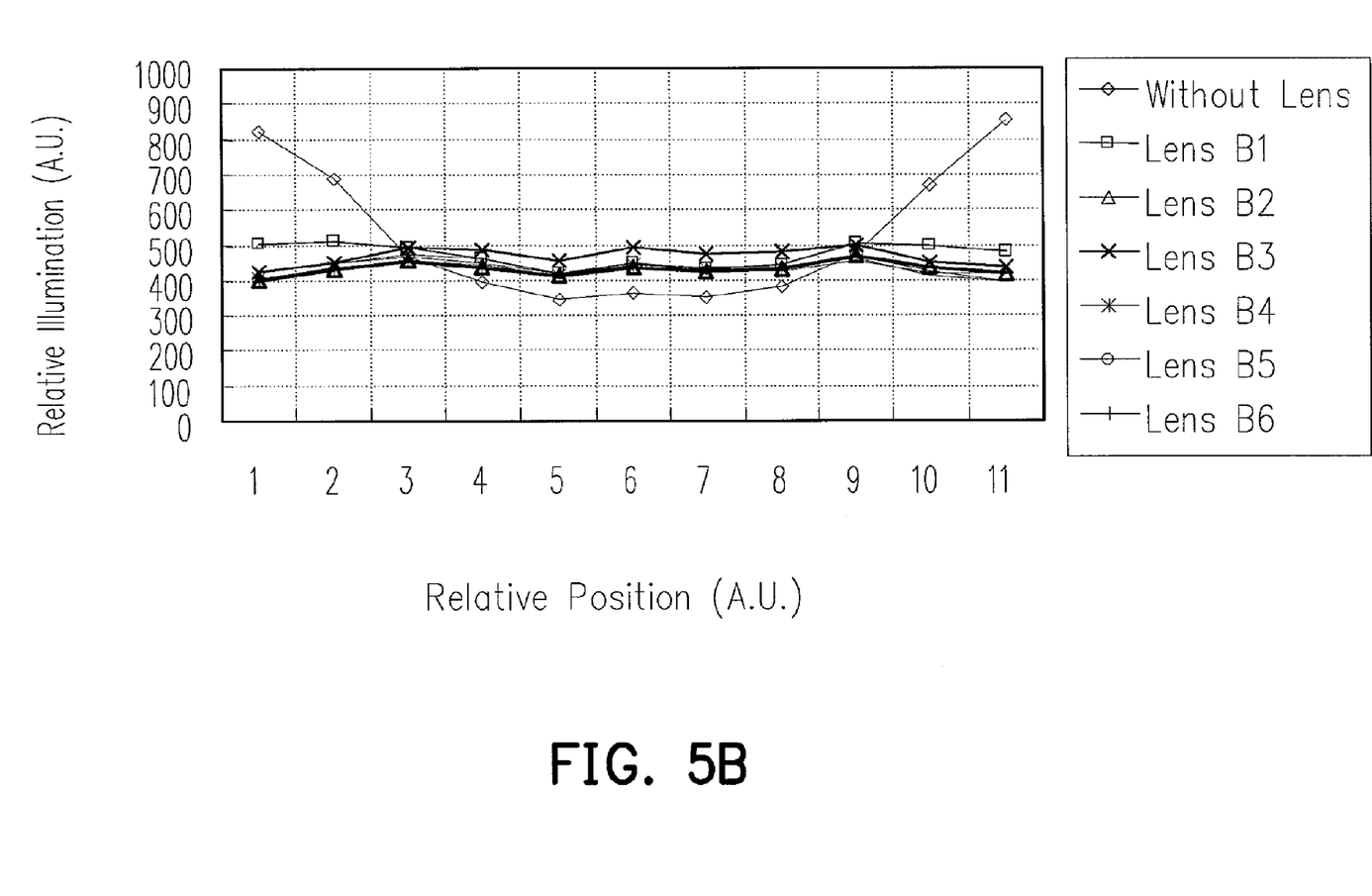
Figure 5C:
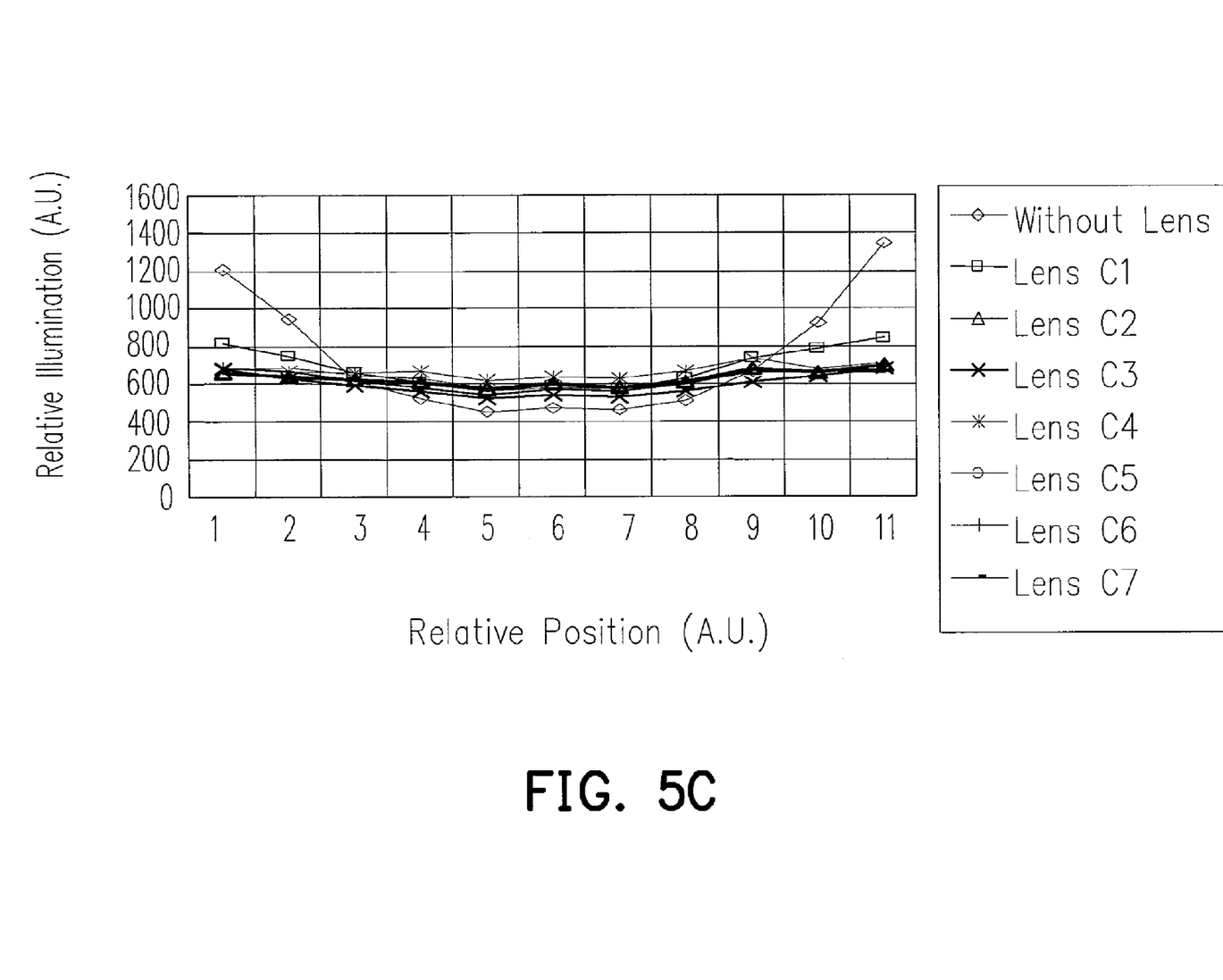
Figure 5D:
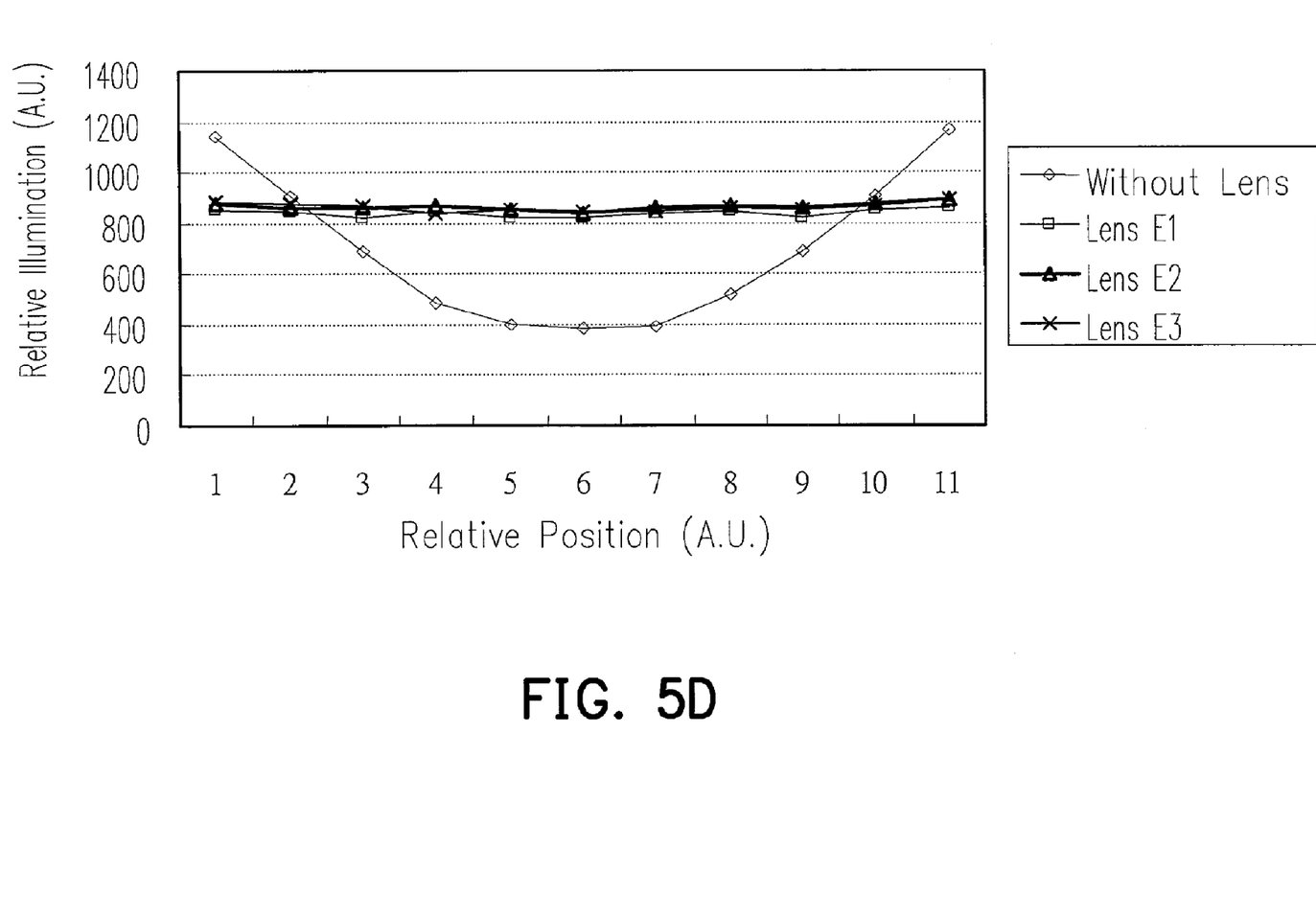

Similarly, FIG. 5B is a diagram showing the illumination distributions obtained by measuring the illumination at the relative positions 1-11 while the light source module 200 has the LEDs with a view angle of 45 degrees and the lenses B1, B2, B3, B4, B5, B6, B7, and B8 of different types. FIG. 5C is a diagram showing the illumination distributions obtained by measuring the illumination at the relative positions 1-11 while the light source module 200 has the LEDs with a view angle of 80 degrees and the lenses C1, C2, C3, C4, C5, C6, C7, and C8 of different types. FIG. 5D is a diagram showing the illumination distributions obtained by measuring the illumination at the relative positions 1-11 while the light source module 200 has the LEDs with a view angle of 120 degrees and the lenses E1, E2, and E3 of different types.

It is known from the illumination distributions shown in FIGS. 5A-5D that the view angle of the LEDs 110 and 210 is not larger than 130 degrees when the brightness of the LEDs 110 and 210 is half of the maximum brightness thereof. In addition, when the view angle of the LEDs 110 and 210 is not larger than 130 degrees, it is possible that similar illumination data are obtained at the relative positions 1-11 while the light source module 200 has the lenses 120 and 220 of a suitable type. Accordingly, uniform illumination distribution is ensured by utilizing the light-coupling light source module 200. That is, the light beams emitted from the light-emitting surface 133 of the side light-emitting flexible light guide rod 130 of the flexible light-emitting apparatus 100 have uniform brightness.

Referring to FIGS. 3 and 4 simultaneously, since the side light-emitting flexible light guide rod 130 of the present embodiment is a rod and is not a plate, the cross section of the side light-emitting flexible light guide rod 130 is a circular, and the side light-emitting flexible light guide rod 130 is able to be bended in any direction perpendicular to an extending direction thereof, so that the side light-emitting flexible light guide rod 130 has better flexibility. Moreover, since light beams emitted from the LEDs are uniformly radiated from the light-emitting surface 133 of the side light-emitting flexible light guide rod 130, the light-emitting directions of the flexible light-emitting apparatus 100 are less limited. Moreover, in addition to favorable polarization properties of the light-emitting layer 135 of the side light-emitting flexible light guide rod 130, the index of refraction of the light-emitting layer 135 relative to the visible light is smaller than the index of refraction of the light guide core 134 relative to the visible light. As a result, while the flexible light-emitting apparatus 100 is bended, light leakage is not apt to occur at bended portions of the flexible light-emitting apparatus. Therefore, even though the flexible light-emitting apparatus 100 is bended, the light beams emitted from the flexible light-emitting apparatus 100 still have highly uniform brightness.

Figure 6:
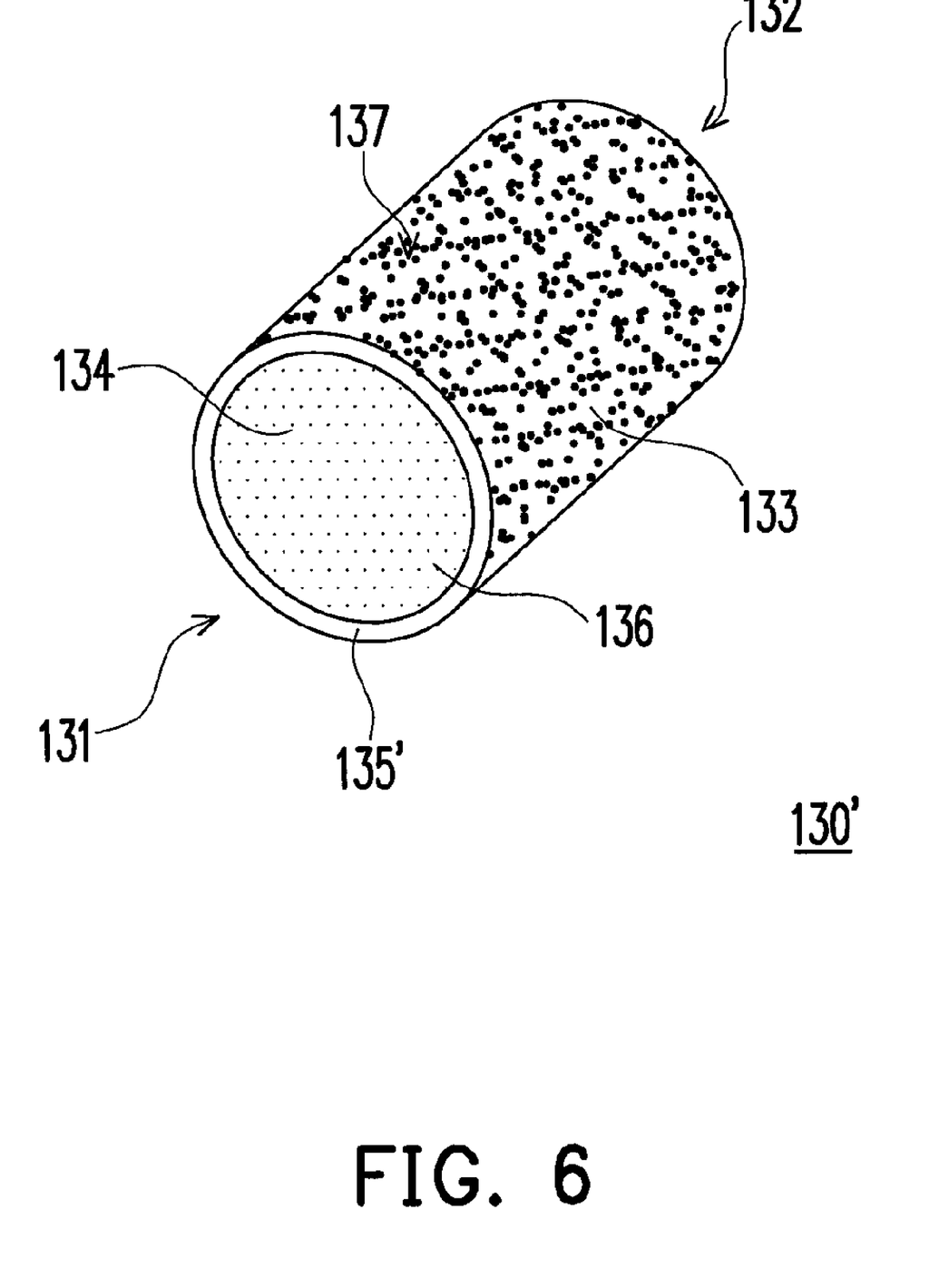
FIG. 6 is a schematic view of a side light-emitting flexible light guide rod according to another embodiment of the present invention.

FIG. 6 is a schematic view of a side light-emitting flexible light guide rod according to another embodiment of the present invention. Referring to FIG. 6, the side light-emitting flexible light guide rod 130' of the present embodiment is similar to the side light-emitting flexible light guide rod 130 shown in FIG. 3, while the main difference therebetween lies in that there are color powders 137 uniformly doped in the light-emitting layer 135 of the side light-emitting flexible light guide rod 130'. Accordingly, the light beams are scattered by the doped color powders 137 and become specific color light beams. After that, the color light beams pass through the light-emitting surface 133 and are transmitted to the outside of the side light-emitting flexible light guide rod 130.

Generally, color light beams emitted from LEDs are only corresponding to specific wavelengths. For example, LEDs available in the market usually emit red light, yellow light, yellow-green light, green light, blue light, or purple light. Besides, optical filters can be employed when light beams with different colors are to be obtained by using white light LEDs without the need of mixing red light, green light, and blue light.

Figure 7A:
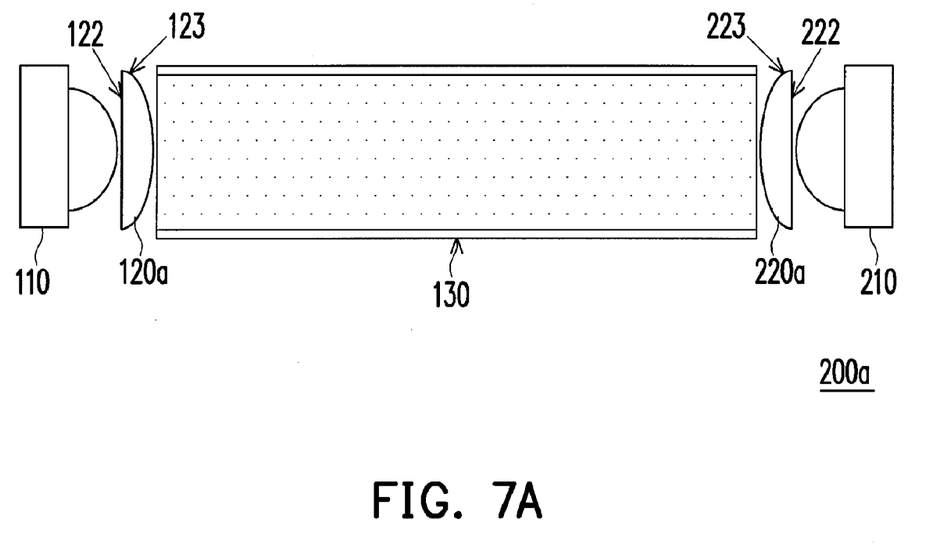
FIG. 7A is a schematic view of a light source module according to another embodiment of the present invention.

FIG. 7A is a schematic view of a light source module according to another embodiment of the present invention.

Referring to FIG. 7A, the light source module 200a of the present embodiment is similar to the light source module 200 shown in FIG. 3, while the main difference therebetween lies in that surfaces 123 and 223 of lenses 120a and 220a are respectively evaporated with an optical thin film. The optical thin films are used to filter color light beams with predetermined wavelengths or let color light beams with predetermined wavelengths pass. In the present embodiment, the LEDs 110 and 210, for example, are the while LEDs, and the lenses 120a and 220a evaporated with the optical thin films serve as two optical filters. As a result, through the lenses 120a and 220a, the color light beams emitted from the LEDs 110 and 210 are filtered and become the color light beams with predetermined wavelengths before entering the side light-emitting flexible light guide rod 130. In other embodiments, it is also likely for surfaces 122 and 222 of the lenses 120a and 220a to be respectively evaporated with the optical thin film.

Figure 7B:
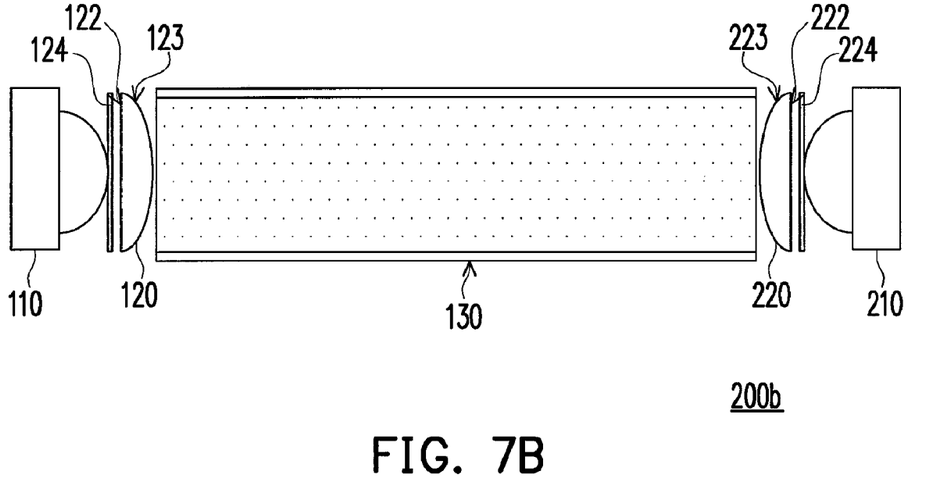
FIG. 7B is a schematic view of a light source module according to another embodiment of the present invention.

FIG. 7B is a schematic view of a light source module according to another embodiment of the present invention. Referring to FIG. 7B, the light source module 200b of the present embodiment is similar to the light source module 200 shown in FIG. 3, while the main difference therebetween lies in that the light source module 200b of the present embodiment further includes two optical filters 124 and 224. The optical filters 124 and 224 are respectively disposed between the LED 110 and the lens 120 and between the LED 210 and the lens 220. Accordingly, through the optical filters 124 and 224, the color light beams emitted from the LEDs 110 and 210 are filtered and become the color light beams with predetermined wavelengths before entering the side light-emitting flexible light guide rod 130.

Figure 7C:
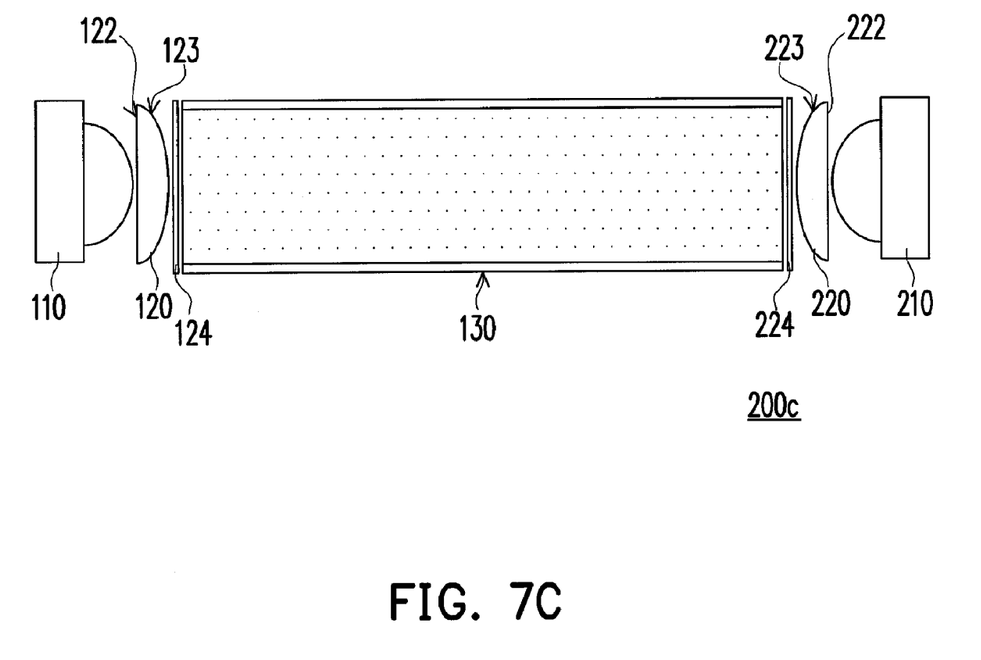
FIG. 7C is a schematic view of a light source module according to another embodiment of the present invention.

FIG. 7C is a schematic view of a light source module according to another embodiment of the present invention. Referring to FIG. 7C, the light source module 200c of the present embodiment is similar to the light source module 200b shown in FIG. 7B, while the main difference therebetween lies in that the optical filters 124 and 224 are respectively disposed between the LED 110 and the side light-emitting flexible light guide rod 130 and between the LED 210 and the side light-emitting flexible light guide rod 130. Similarly, through the optical filters 124 and 224, the color light beams emitted from the LEDs 110 and 210 are filtered and become the color light beams with predetermined wavelengths before entering the side light-emitting flexible light guide rod 130.

Figure 8A:
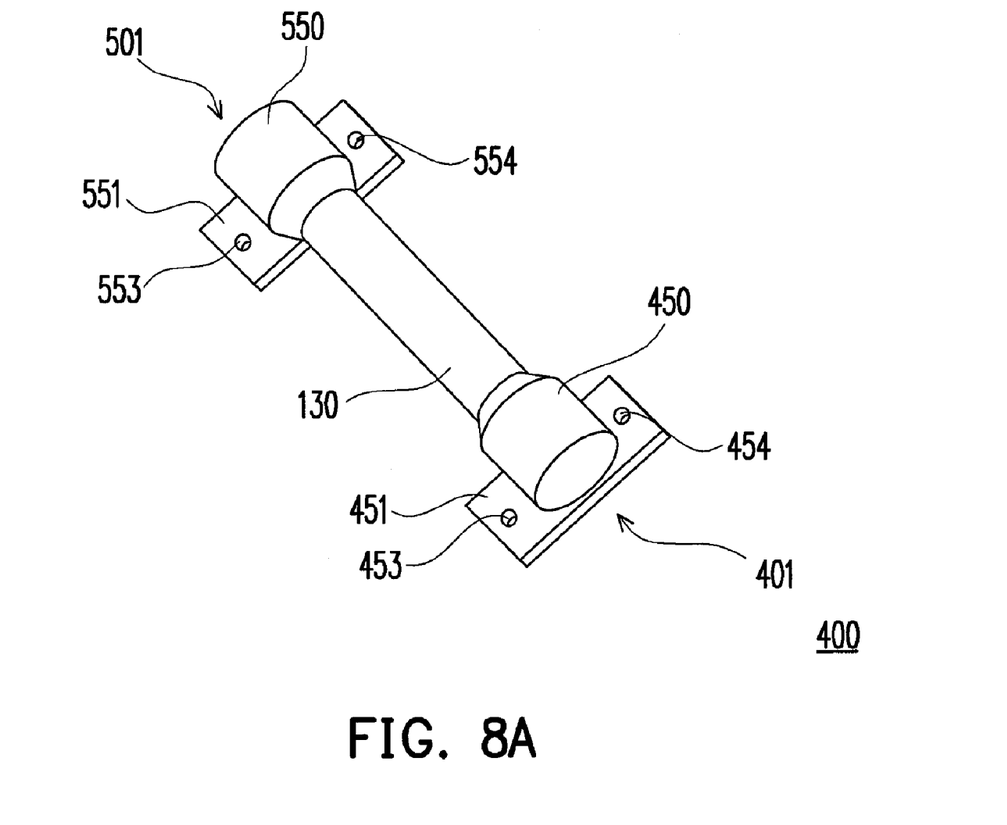
FIGS. 8A and 8B are respectively a three-dimensional view and a top view of a flexible light-emitting apparatus according to another embodiment of the present invention.
Figure 8B:
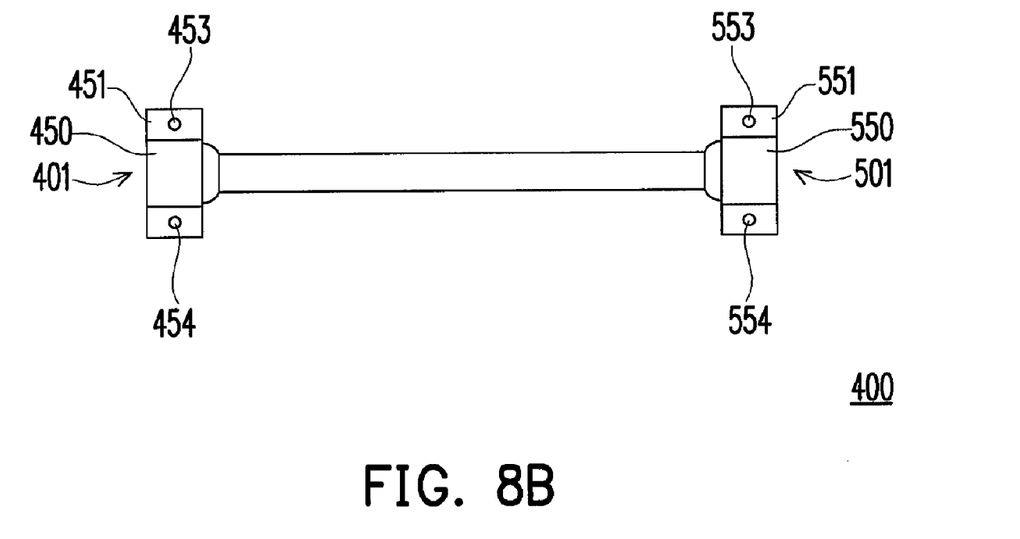

FIGS. 8A and 8B are respectively a three-dimensional view and a top view of a flexible light-emitting apparatus 400 according to another embodiment of the present invention. Referring FIGS. 8A and 8B, the flexible light-emitting apparatus 400 of the present embodiment is similar to the flexible light-emitting apparatus 100 shown in FIG. 2, while the main difference therebetween lies in that the flexible light-emitting apparatus 400 of the present embodiment further includes two mounting bases 451 and 553, wherein each of the mounting bases 451 and 553 is respectively connected to the corresponding package housing. In the present embodiment, the mounting bases 451 and 553 respectively include screw holes 453 and 454 and screw holes 553 and 554.

As a result, through the mounting bases 451 and 553, the flexible light-emitting apparatus 400 is able to be fixed on a specific foundation. Accordingly, heat generated by the LEDs not only can be directly released from surfaces 450 and 550 of the package housings 401 and 501 to the environment but also can be conducted through the surfaces 450 and 550 of the package housings 401 and 501 to the mounting bases 451 and 553 and the specific foundation and further to the environment. Moreover, after the package housings 401 and 501 and the side light-emitting flexible light guide rod 130 are assembled, while the flexible light-emitting apparatus 400 is bended to be in a certain shape, centers of the package housings 401 and 501 and the side light-emitting flexible light guide rod 130 stay on a light axis without being shifted. In other embodiments, the mounting bases can be integrally formed with the corresponding package housing.

In view of the above, the flexible light-emitting apparatus of the embodiments of the present invention utilizes the side light-emitting flexible light guide rod to guide light beams, and the LEDs are respectively disposed at the two ends of the side light-emitting flexible light guide rod. Since the side light-emitting flexible light guide rod is a rod and is not a plate, the side light-emitting flexible light guide rod is able to be bended in any direction perpendicular to the extending direction thereof, so that the side light-emitting flexible light guide rod has better flexibility. Moreover, since light beams emitted from the LEDs are uniformly radiated from the light-emitting surface of the side light-emitting flexible light guide rod, the light-emitting directions of the side light-emitting flexible light guide rod are less limited. Besides, in the side light-emitting flexible light guide rod of the embodiments of the present invention, while the flexible light-emitting apparatus is bended, light leakage is not apt to occur at the bended portion of the flexible light-emitting apparatus. Therefore, even though the flexible light-emitting apparatus of the embodiments of the present invention is bended, the light beams emitted from the flexible light-emitting apparatus can still have highly uniform brightness.

Although the invention has been described with reference to a particular embodiment thereof, it will be apparent to one of the ordinary skills in the art that modifications to the described embodiment may be made without departing from the spirit of the invention. Accordingly, the scope of the invention will be defined by the attached claims not by the above detailed description.

What is claimed is:

1. A flexible light-emitting apparatus, comprising:
   a side light-emitting flexible light guide rod having a first end, a second end opposite to the first end, and a light-emitting surface connecting the first and the second ends, the side light-emitting flexible light guide rod comprising:
     a light guide core extending from the first end to the second end of the side light-emitting flexible light guide rod, wherein grains of methyl methacrylate styrene (MS) having a diameter of 6-15 micrometers and a weight percentage of 0.01%-0.03% are doped into and uniformly distributed in the light guide core; and
     a light-emitting layer surrounding the light guide core and extending from the first end to the second end of the side light-emitting flexible light guide rod, wherein an index of refraction of the light guide core relative to a visible light is larger than an index of refraction of the light-emitting layer relative to the visible light;
   two light emitting diodes (LEDs) respectively disposed beside the first end and the second end and adapted to emit a light beam toward the side light-emitting flexible light guide rod respectively; and
   two lenses, one of the lenses being located between the first end and the LED disposed beside the first end, the other one of the lenses being located between the second end and the LED disposed beside the second end,
   wherein each of the light beams respectively enters the side light-emitting flexible light guide rod through the corresponding lens and is transmitted to the outside of the side light-emitting flexible light guide rod through the light-emitting surface.

2. The flexible light-emitting apparatus as claimed in claim 1, wherein when a brightness of the LEDs is half of a maximum brightness thereof, a view angle of the LEDs is not larger than 130 degrees.

3. The flexible light-emitting apparatus as claimed in claim 1, wherein the lenses have a function of focusing the light beams, and focus lengths thereof are not longer than 20 millimeters.

4. The flexible light-emitting apparatus as claimed in claim 1, wherein a material of the lenses is glass, plastic, or resin.

5. The flexible light-emitting apparatus as claimed in claim 1, wherein a surface of each of the lenses is respectively evaporated with an optical thin film, and the optical thin films are used to filter color light beams with predetermined wavelengths or let color light beams with predetermined wavelengths pass.

6. The flexible light-emitting apparatus as claimed in claim 1, wherein a distance between each of the lenses and the LED corresponding thereto is not longer than 1.5 millimeters.

7. The flexible light-emitting apparatus as claimed in claim 1, further comprising two optical filters, wherein each of the optical filters is respectively disposed between one of the lenses and the LED corresponding thereto or between the lens and the side light-emitting flexible light guide rod.

8. The flexible light-emitting apparatus as claimed in claim 1, wherein a distance between each of the lenses and the side light-emitting flexible light guide rod is not longer than 1.5 millimeters.

9. The flexible light-emitting apparatus as claimed in claim 1, wherein a material of the light guide core is a copolymer $MMA_xBMA_y3EGDMA_{1-x-y}$ formed by methyl methacrylate (MMA), normal butyl(bornyl)methacrylate (BMA), and tri-ethylene glycol dimethacrylate (3EGDMA) in different proportions, x and y are positive numbers, and $0.22 \leq x \leq 0.35$ and $0.45 \leq y \leq 0.63$.

10. The flexible light-emitting apparatus as claimed in claim 1, wherein a material of the light-emitting layer is tetra-fluoro-ethylene, perfluoro-alkoxy, or fluorinated propylene ethylene.

11. The flexible light-emitting apparatus as claimed in claim 1, wherein the light-emitting layer has color powders.

12. The flexible light-emitting apparatus as claimed in claim 1, further comprising two package housings, each of the package housings being respectively used to house one of the LEDs and the lens corresponding thereto.

13. The flexible light-emitting apparatus as claimed in claim 12, further comprising two mounting bases, each of the mounting bases being respectively connected to the corresponding package housing, so that the package housings are fixed onto a foundation by bending the mounting bases, wherein heat generated by the LEDs is released through the foundation to the environment.

14. The flexible light-emitting apparatus as claimed in claim 13, wherein each of the mounting bases is integrally formed with the corresponding package housing.

* * * * *